US012567124B2

(12) United States Patent
Landvater

(10) Patent No.: US 12,567,124 B2
(45) Date of Patent: Mar. 3, 2026

(54) TECHNOLOGIES FOR IMPROVED WHOLE SLIDE IMAGING

(71) Applicant: THE REGENTS OF THE UNIVERSITY OF MICHIGAN, Ann Arbor, MI (US)

(72) Inventor: Ryan Landvater, Ypsilanti, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 407 days.

(21) Appl. No.: 18/134,086

(22) Filed: Apr. 13, 2023

(65) Prior Publication Data

US 2023/0334621 A1 Oct. 19, 2023

Related U.S. Application Data

(60) Provisional application No. 63/330,611, filed on Apr. 13, 2022.

(51) Int. Cl.
| | |
|---|---|
| *G06T 3/40* | (2024.01) |
| *G06T 1/20* | (2006.01) |
| *G06T 1/60* | (2006.01) |
| *G16H 30/40* | (2018.01) |

(52) U.S. Cl.
CPC .................. *G06T 3/40* (2013.01); *G06T 1/20* (2013.01); *G06T 1/60* (2013.01); *G16H 30/40* (2018.01); *G06T 2200/24* (2013.01)

(58) Field of Classification Search
CPC .... G06T 3/40; G06T 1/20; G06T 1/60; G06T 2200/24; G06T 11/40; G16H 30/40;
(Continued)

(56) References Cited

U.S. PATENT DOCUMENTS

| | | | |
|---|---|---|---|
| 7,554,543 B2 * | 6/2009 | Aguera Y Arcas | ... G06F 3/0481 |
| | | | 345/428 |
| 7,826,649 B2 | 11/2010 | Crandall et al. | |

(Continued)

OTHER PUBLICATIONS

Rolls, Geoffrey, "An Introduction to Specimen Processing," *Leica Biosystems*, (2024).

(Continued)

*Primary Examiner* — James A Thompson
*Assistant Examiner* — Kim Tranh T Tran
(74) *Attorney, Agent, or Firm* — MARSHALL, GERSTEIN & BORUN LLP

(57) ABSTRACT

Technologies for improved whole slide imaging (WSI) are disclosed. An example method includes receiving a whole slide image file comprised of image data corresponding to a tissue sample, wherein the whole slide image file includes one or more resolution layers that each include one or more tiles. The example method further includes determining a current view region of a portion of the whole slide image file at a user interface, and determining a tile status for each tile within the current view region. The example method further includes subdividing buffering requirements into one or more buffering transactions, wherein each buffering transaction corresponds to at least one tile of the one or more tiles within the current buffer region that has a cached tile status; and rendering, at the user interface, each tile within the current view region with an already buffered tile status for viewing by a user.

20 Claims, 5 Drawing Sheets

(58) Field of Classification Search
     CPC ........ G16H 30/20; G16H 40/60; G16H 50/20;
     G16H 70/60
     USPC ........................................................ 345/428
     See application file for complete search history.

(56)                    References Cited

U.S. PATENT DOCUMENTS

| 8,582,849 | B2 | 11/2013 | Eichhorn et al. | |
|---|---|---|---|---|
| 8,724,914 | B2 * | 5/2014 | Inada | G06T 11/00 |
| | | | | 382/250 |
| 2004/0175059 | A1 * | 9/2004 | Willner | H04N 21/234327 |
| | | | | 382/305 |
| 2015/0070357 | A1 * | 3/2015 | Tahan | G06F 3/14 |
| | | | | 345/428 |
| 2016/0227248 | A1 * | 8/2016 | Choi | H04N 19/70 |
| 2024/0086460 | A1 * | 3/2024 | Ben Shaul | G16H 30/40 |
| 2025/0156987 | A1 * | 5/2025 | Kirszenberg | H04N 23/58 |

OTHER PUBLICATIONS

Mukhopadhyay et al., "Whole Slide Imaging Versus Microscopy for Primary Diagnosis in Surgical Pathology," *The American Journal of Surgical Pathology*, vol. 42, No. 1 (2018).

Melo et al., "Whole Slide Imaging and Its Applications to Histopathological Studies of Liver Disorders," *frontiers in Medicine*, vol. 6 (2020).
"Whole Slide Imaging: A Crach Course," *Reveal Biosciences* (2019).
Kim et al., "Defining the High-Power Field for Digital Pathology," *Journal of Pathology Informatics* (2020).
Wienert et al., "Integration and acceleration of virtual microscopy as the key to successful implementation into the routine diagnostic process," *Diagn Pathol.*, (2009).
Couture, H., From Patches to Slides: How to Train Deep Learning Models on Gigapixel Imagies With Weak Supervision, *Towards Data Science*, (2021).
Kumar et al., "Whole Slide Imaging (WSI) in Pathology: Current Perspectives and Future Directions," *Journal of Digital Imaging*, vol. 33 (2020).
Muñoz-Aguirre et al., "PyHIST: A Histological Image Segmentation Tool," *PLOS Computational Biology*, (2020).
Vo et al., "MaRelA: A Cloud MapReduce Based High Performance Whole Slide Image Analysis Framework," *Distrib Parallel Databases*, (2019).
Schuffler et al., "FlexTileSource: An OpenSeadragon Extension for Efficient Whole-Slide Image Visualization," *J. Pathol Inform*, (2021).

* cited by examiner

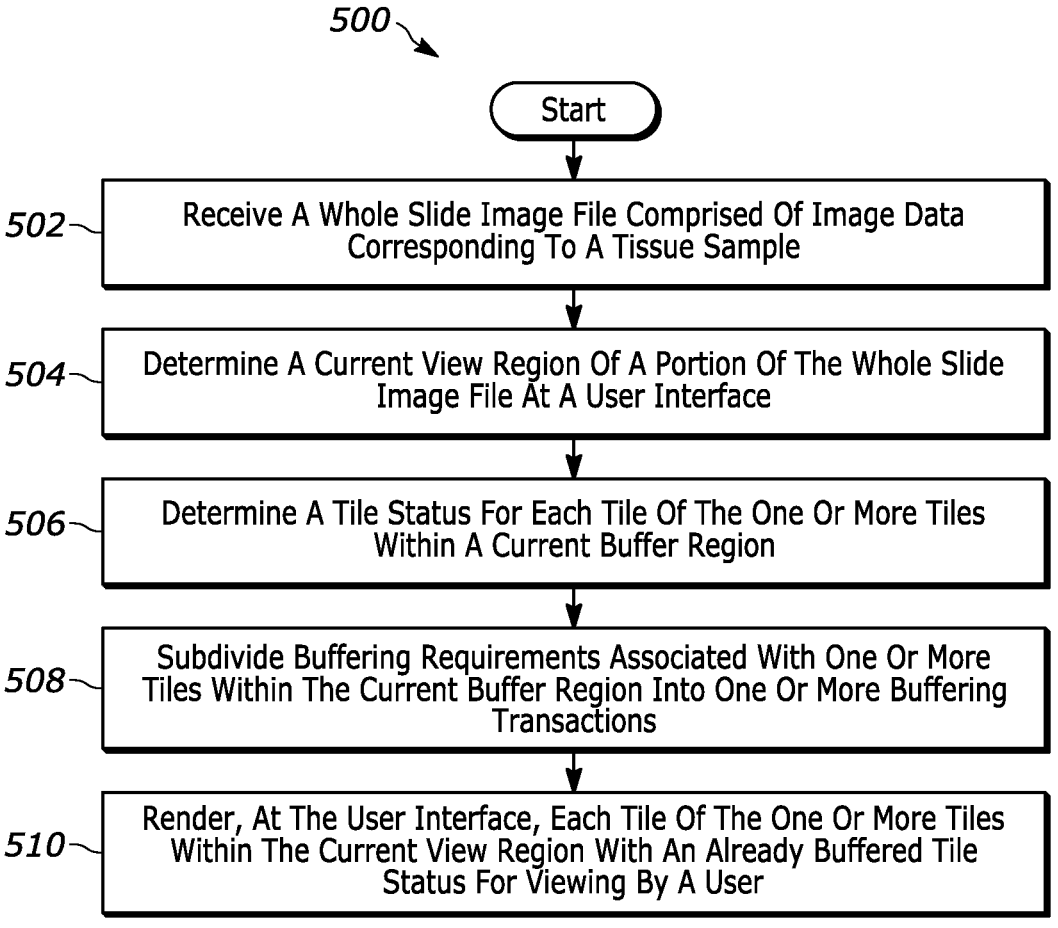

*500*

Start

502 — Receive A Whole Slide Image File Comprised Of Image Data Corresponding To A Tissue Sample 504 — Determine A Current View Region Of A Portion Of The Whole Slide Image File At A User Interface 506 — Determine A Tile Status For Each Tile Of The One Or More Tiles Within A Current Buffer Region 508 — Subdivide Buffering Requirements Associated With One Or More Tiles Within The Current Buffer Region Into One Or More Buffering Transactions 510 — Render, At The User Interface, Each Tile Of The One Or More Tiles Within The Current View Region With An Already Buffered Tile Status For Viewing By A User

FIG. 5

TECHNOLOGIES FOR IMPROVED WHOLE SLIDE IMAGING

CROSS-REFERENCE TO RELATED APPLICATION

This application claims priority to U.S. Provisional Patent Application No. 63/330,611, entitled "Technologies for Improved Whole Slide Imaging," filed on Apr. 13, 2022, the disclosure of which is hereby incorporated herein by reference.

FIELD OF THE DISCLOSURE

The present disclosure relates generally to whole slide imaging (WSI) and, more particularly, to technologies for improved WSI.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

Conventional histopathology is the analysis of cell or tissue samples by standard light or fluorescence microscopy, and is an indispensable tool for the diagnosis of disease. Generally, histopathology involves processing a tissue sample removed from a patient in order to create incredibly thin sections of the tissue sample that are mounted onto a glass slide. These thin sections of tissue are then stained with a staining protocol that is appropriate for the tissue being imaged and the disease or abnormality under investigation. Once stained, a pathologist images the tissue sections using light or fluorescent microscopy for diagnosis.

In particular, digital histopathology, also called whole slide imaging (WSI), is a tool of rapidly evolving importance within the discipline of pathology. Generally speaking, digital histopathology involves the rendering, transfer, and/ or storage of tissue sections in a computer (e.g., byte) format that can be analyzed by a pathologist via a computer monitor. Digital histopathology has the potential to greatly improve over conventional histopathology techniques through advanced computer-vision analysis, rapid quantification, digital permanence, and ease of consultation. Unfortunately, the implementation and adoption of digital histopathology is limited by a relative difficulty of use and slow speed of high-quality image delivery, and as a consequence, many pathologists continue to use conventional techniques.

The problem is particularly acute because, for pathologists, practical adoption of digital histopathology requires comparable speed, resolution, and ease of use relative to a microscope, which is currently unavailable with digital histopathology systems. High-resolution (e.g., high-DPI) image rendering of the type needed to discern regions of interest at low power or subtle cytologic characteristics of cells, requires large amounts of image data. Additionally, such image rendering requires appropriate image scaling and subsampling to avoid visual artifacts (e.g., Moiré fringes) and distortion. A tile-based rendering technique, where a large image is broken into multiple smaller images (referenced herein as "tiles" and "image tiles"), is a practical approach that provides these speed and clarity characteristics required to replace conventional histology techniques.

However, WSI viewing is unlike other image applications, at least in that a typical compressed slide image exceeds 1 gigabyte (GB) in size, which causes multiple problems for conventional image viewers. A conventional image viewer attempting to precache such an image would take well over a minute per slide, and would regularly exceed the hardware limits of most computers available to pathologists, thereby rendering prechaching impractical. Moreover, conventional image viewers that are capable of buffering images in a tile-based format or responding to unpredictable user movement fail to provide the clarity necessary for pathologists to reliably diagnose conditions from the slides. More specifically, conventional image viewers fail to buffer images in a manner that provides the appropriate bandwidth and subsampling to ensure rapid, relevant image rendering without visual artifacts that is comparable to physical slide movement under a microscope.

Therefore, there is a need for improved WSI technologies that provide the clarity and speed necessary for pathologists to easily, quickly, and accurately evaluate images in a manner that improves diagnostic capabilities.

SUMMARY OF THE INVENTION

According to an aspect of the present disclosure, a method for improved whole slide imaging (WSI) is disclosed. The method comprises: receiving, at one or more processors, a whole slide image file comprised of image data corresponding to a tissue sample, the whole slide image file including one or more resolution layers that each include one or more tiles; determining, by the one or more processors, a current view region of a portion of the whole slide image file at a user interface; (a) determining, by the one or more processors, a tile status for each tile of the one or more tiles within a current buffer region; (b) subdividing, by the one or more processors, buffering requirements associated with one or more tiles within the current buffer region into one or more buffering transactions, wherein each buffering transaction corresponds to at least one tile of the one or more tiles within the current buffer region that has a cached tile status; and (c) rendering, at the user interface, each tile of the one or more tiles within the current view region with an already buffered tile status for viewing by a user.

In a variation of this embodiment, the method further comprises: detecting, by the one or more processors, that the user has adjusted the current view region to a new current view region of a new portion of the whole slide image file within the user interface; designating, by the one or more processors, the current view region as a subsequent view region and the new current view region as the current view region; and performing each of steps (a)-(c) based on the current view region.

In another variation of this embodiment, each tile of the one or more tiles within the current view region corresponds to a high resolution layer of the one or more resolution layers, and the method further comprises: responsive to at least one tile of the one or more tiles within the current view region having an un-cached tile status, rendering, at the user interface, at least a portion of a corresponding lower resolution tile with an already buffered tile status for viewing by a user in place of the at least one tile.

In yet another variation of this embodiment, each tile of the one or more tiles within the current buffer region corresponds to a high resolution layer of the one or more resolution layers, and the method further comprises: subdividing, by the one or more processors, the buffering requirements associated with the one or more tiles within the current buffer region into one or more buffering transactions, such that each tile of one or more lower resolution tiles within the current buffer region that has a cached tile status is buffered prior to buffering each tile of the one or more tiles within the current buffer region that has a cached tile status.

In still another variation of this embodiment, the method further comprises: dividing, by the one or more processors, a display screen used to display the user interface into one or more rendering layers; and subdividing, by the one or more processors, each rendering layer of the one or more rendering layers into one or more rendering tiles. Further in this variation, the one or more resolution layers includes a first number of layers, and the one or more rendering layers includes a second number of layers that is different from the first number of layers.

In yet another variation of this embodiment, the method further comprises: dividing, by the one or more processors, the whole slide image file into the one or more resolution layers; and subdividing, by the one or more processors, each resolution layer of the one or more resolution layers into one or more tiles based on a number of pixels included in a respective resolution layer.

In still another variation of this embodiment, the method further comprises: assigning, by the one or more processors, a cache address in a local memory to each tile of the one or more tiles for each resolution layer of the one or more resolution layers.

In yet another variation of this embodiment, the method further comprises: buffering, by the one or more processors, each tile of the one or more tiles within the current buffer region that has the cached tile status; uploading, by the one or more processors, each buffered tile to a graphics processing unit (GPU); and subsampling, by the GPU, each buffered tile.

In still another variation of this embodiment, the method further comprises: (a) determining, by the one or more processors, a tile status for each tile of the one or more tiles within the current buffer region, wherein an un-cached tile status indicates that the associated tile is not yet loaded into a random access memory (RAM), the cached tile status indicates that the associated tile is loaded into the RAM and not yet buffered for uploading to a graphics processing unit (GPU), and the already buffered tile status indicates that the associated tile is buffered and loaded to the GPU for rendering at the user interface.

In another embodiment, a system for improved whole slide imaging (WSI) is disclosed. The system comprises: a user interface; a memory storing a set of computer-readable instructions; and a processor interfacing with the user interface and the memory, and configured to execute the set of computer-readable instructions to cause the processor to: receive a whole slide image file comprised of image data corresponding to a tissue sample, the whole slide image file including one or more resolution layers that each include one or more tiles, determine a current view region of a portion of the whole slide image file at a user interface, (a) determine a tile status for each tile of the one or more tiles within a current buffer region, (b) subdivide buffering requirements associated with one or more tiles within the current buffer region into one or more buffering transactions, wherein each buffering transaction corresponds to at least one tile of the one or more tiles within the current buffer region that has a cached tile status, and (c) render, at the user interface, each tile of the one or more tiles within the current view region with an already buffered tile status for viewing by a user.

In a variation of this embodiment, the set of computer-readable instructions, when executed, further cause the processor to: detect that the user has adjusted the current view region to a new current view region of a new portion of the whole slide image file within the user interface; designate the current view region as a subsequent view region and the new current view region as the current view region; and perform each of steps (a)-(c) based on the current view region.

In another variation of this embodiment, each tile of the one or more tiles within the current view region corresponds to a high resolution layer of the one or more resolution layers, and the set of computer-readable instructions, when executed, further cause the processor to: subdivide the buffering requirements associated with the one or more tiles within the current buffer region into one or more buffering transactions, such that each tile of one or more lower resolution tiles within the current buffer region that has a cached tile status is buffered prior to buffering each tile of the one or more tiles within the current buffer region that has a cached tile status; and responsive to at least one tile of the one or more tiles within the current view region having an un-cached tile status, render, at the user interface, at least a portion of a corresponding lower resolution tile with an already buffered tile status for viewing by a user in place of the at least one tile.

In yet another variation of this embodiment, the set of computer-readable instructions, when executed, further cause the processor to: divide a display screen used to display the user interface into one or more rendering layers; and subdivide each rendering layer of the one or more rendering layers into one or more rendering tiles. Further in this variation, the one or more resolution layers includes a first number of layers, and the one or more rendering layers includes a second number of layers that is different from the first number of layers.

In still another variation of this embodiment, the set of computer-readable instructions, when executed, further cause the processor to: divide the whole slide image file into the one or more resolution layers; and subdivide each resolution layer of the one or more resolution layers into one or more tiles based on a number of pixels included in a respective resolution layer.

In yet another variation of this embodiment, the set of computer-readable instructions, when executed, further cause the processor to: assign a cache address in a local memory to each tile of the one or more tiles for each resolution layer of the one or more resolution layers.

In still another variation of this embodiment, the set of computer-readable instructions, when executed, further cause the processor to: buffer each tile of the one or more tiles within the current buffer region that has the cached tile status; upload each buffered tile to a graphics processing unit (GPU); and cause the GPU to subsample each buffered tile.

In yet another variation of this embodiment, the set of computer-readable instructions, when executed, further cause the processor to: (a) determine a tile status for each tile of the one or more tiles within the current buffer region, wherein an un-cached tile status indicates that the associated tile is not yet loaded into a random access memory (RAM), the cached tile status indicates that the associated tile is loaded into the RAM and not yet buffered for uploading to a graphics processing unit (GPU), and the already buffered tile status indicates that the associated tile is buffered and loaded to the GPU for rendering at the user interface.

In yet another embodiment, a non-transitory computer-readable storage medium having stored thereon a set of instructions, executable by at least one processor, for improved whole slide imaging (WSI) is disclosed. The instructions comprise: instructions for receiving a whole slide image file comprised of image data corresponding to a tissue sample, the whole slide image file including one or more resolution layers that each include one or more tiles; instructions for determining a current view region of a portion of the whole slide image file at a user interface; instructions for determining a tile status for each tile of the one or more tiles within a current buffer region; instructions for subdividing buffering requirements associated with one or more tiles within the current buffer region into one or more buffering transactions, wherein each buffering transaction corresponds to at least one tile of the one or more tiles within the current buffer region that has a cached tile status; and instructions for rendering, at the user interface, each tile of the one or more tiles within the current view region with an already buffered tile status for viewing by a user.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

FIG. 5 illustrates an example method for improved WSI, in accordance various aspects disclosed herein.

DETAILED DESCRIPTION

Figure 1:
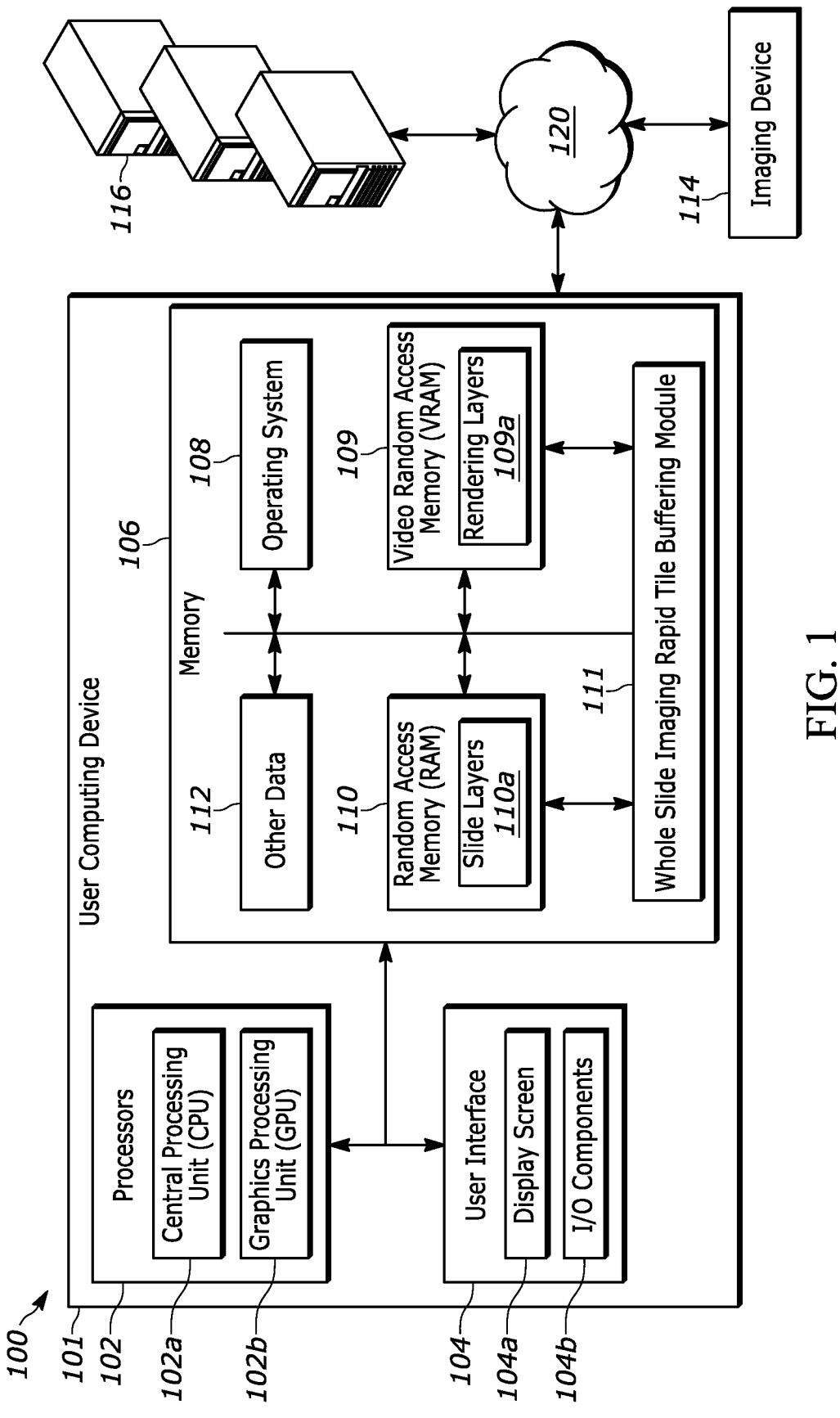
FIG. 1 illustrates an example computing environment for improved whole slide imaging (WSI), in accordance various aspects disclosed herein.

As previously mentioned, digital histopathology, also called whole slide imaging (WSI), is the process of digitally acquiring high resolution images of an entire section of stained tissue mounted on a glass slide that can then be analyzed by a pathologist via a computer monitor. In general, there are two main processes associated with WSI: (1) digitizing an entire glass slide containing a mounted tissue section using specialized hardware, and (2) viewing and analysis of the digital image using specialized software. The digitizing process typically involves a whole slide scanner, which is essentially a microscope with a built-in camera specifically configured to capture images of slides.

More specifically, the whole slide scanner may capture images of the entire slide by capturing a series of images (e.g., "tiles"). Many modern scanners may instead utilize a scanline approach by capturing a continuous stream of images across the slide. This scanline approach may result in faster image capture times when compared with the discretized tile approach, but can suffer from lower quality image resolution. Regardless, when the scanner captures a series of tiles representing the slide, the imaging software then stitches the tiles together to produce a high resolution image of the entire tissue section mounted on the slide. This stitched image may then be viewed by a pathologist, or other practitioner, in order to diagnose conditions evident in the tissue sample represented by the digital images.

As a result of this WSI methodology, the field of pathology has received numerous benefits. First, whole slide images enable the indefinite preservation of the staining and tissue quality at the time of the scan because the images are stored digitally, as opposed to the conventional physical storage of the tissue slides. Conventional glass slides, even when well preserved, can break and/or degrade in quality over time. This results in a loss of information for both the corresponding patient and for research and educational purposes. Additionally, this indefinite preservation is important for the diagnosis of recurrent/metastatic disease. Pathologists can currently request primary material (e.g., at time of frozen section or in transfer cases), but having immediate digital access to a patient's prior slides or to example cases of a certain diagnosis, as is possible with WSI, greatly improves clinical accuracy.

Second, the whole slide images are easier and faster to share than conventional slides. If a pathologist needs/wants a second opinion or requires the expertise of a specialist, then the pathologist generally requires access to the corresponding slides for analysis. Conventional glass slides must be securely packaged and shipped, which is time consuming and incurs the additional risk of damaging the slides at some point in transit. By contrast, whole slide images can allow for a faster turnaround time for analysis and diagnosis, at least because the slides are digitally retrievable, and are thereby more difficult to misplace or lose.

Third, WSI allows for continued development of new tools to aid in the viewing and analyzing of digitized slides. The computational analysis of whole slide images enabled by digital imaging and uploading of the slides allows for an increase in objective and quantitative data analysis of the tissues represented in the images. Deep neural networks/ machine learning models can be trained to process whole slide images to aid researchers and pathologists in analysis and diagnosis. Moreover, beyond primary diagnosis, these computational advantages may also result in increased pathologist efficiency through the rapid identification of mitoses, enumeration of features (mitosis per field, positively staining cells, percentage of slide that has some feature), and other features that conventional techniques are unable to provide. Further, annotations can be added directly to the digital images, which is beneficial for both presentation and education purposes, and can improve over conventional physical markings.

Fourth, whole slide images take up almost no physical space in the research laboratory or pathology department, unlike conventional glass slides. Conventional glass slides must be stored for preservation purposes, and this storage can take up substantial space that many laboratories or pathology departments may simply not have available. Accordingly, digital whole slide images solve this problem entirely by completely removing the dependence on physical slides, and thereby enables the laboratories and pathology departments to allocate their available space to more important needs.

However, WSI also suffers from several drawbacks that have resulted in a low adoption rate of WSI within the pathology field, as previously discussed. For example, the cost alone of purchasing the necessary equipment, training personnel for collecting and analyzing WSIs, digital slide storage systems, regulatory/licensing costs, and incorporating WSI into previously established histopathology protocols all contribute to an exceedingly high upfront cost that drives many prospective users away. Upfront costs aside, the practical realities of implementing WSI on a day-to-day basis can be daunting for many practitioners.

WSI requires very high resolution images that can take a significant amount of time to capture and process. Typically, the scan time required to image a biopsy tissue sample may range from 1-5 minutes per slide, and tissue samples from a surgical specimen may take 5-20 minutes per slide. Such long scan times can minimize the beneficial impacts of WSI, as a practitioner may take a substantial time to reach a diagnosis while waiting for the slides to process. Additionally, these image files may be hundreds of megabytes/gigabytes in size, which can make the data difficult to store digitally, and digital compression can only be minimally applied before data loss eliminates the utility of the digital images for diagnosis purposes. Moreover, differences in display equipment (e.g., resolution and size of digital computer monitors) often influence how well scanned images are reconstructed for analysis. Taken as a whole, these difficulties cause many practitioners to avoid WSI entirely in favor of the conventional slide analysis techniques.

In order to alleviate these, and other, problems, the present disclosure provides techniques for improved WSI. Generally, the techniques described herein begin by subdividing slides into multiple resolution layers (e.g., layers at different magnifications). Each resolution layer is then subdivided into a series of sub-images (e.g., "tiles") that are each assigned a cache address in local random-access memory (RAM). As a result, each cached and decompressed tile is immediately available for graphics processing unit (GPU) buffering transactions. When a particular tile is located within a portion of the slide that is currently being viewed by a user (e.g., within the dimensions of the user's display), the GPU may dynamically allocate resources to upload the tile to video random-access memory (VRAM) for rendering on the user's display. The mapping between tile indices and the GPU resources is dynamically updated as tiles enter/exit the viewing region of the user's display, such that the GPU resources are dynamically reallocated as part of the buffering sequence.

As a result of the techniques disclosed herein, the issues commonly associated with WSI data collection, storage, operator (pathologist) efficiency, and technology adoption are minimized. In particular, the present techniques solve the buffering and image clarity problems experienced by conventional techniques by fragmenting both the image and upload process into numerous small transactions. These transactions are highly transient (e.g., short-lived) and immediately relevant to the pathologist's user experience. User assumptions and data bandwidth requirements are also minimized by eliminating unnecessary buffering transactions, such that the saved bandwidth can be reallocated to higher fidelity/higher-DPI resources. Additionally, computationally intensive subsampling transactions are performed only on visible images and are parallelized to further minimize the strain on computational resources.

Thus, in accordance with the discussions herein, the present disclosure includes improvements to other technologies or technical fields at least because the present disclosure describes or introduces improvements in the field of digital histopathology. Namely, the whole slide imaging rapid tile buffering module executing on the user computing device or other computing devices (e.g., external server) improves the field of digital histopathology by increasing the speed of buffering and rendering tasks for WSIs in a manner that was previously unachievable using conventional techniques. This improves over conventional techniques at least because such techniques lack the ability to perform the buffering/rendering sequences performed as a result of the instructions included in the whole slide imaging rapid tile buffering module, and are otherwise simply not capable of performing WSI buffering/rendering in a manner similar to the techniques of the present disclosure.

In addition, the present disclosure includes specific features other than what is well-understood, routine, conventional activity in the field, or adding unconventional steps that confine the claim to a particular useful application, e.g., determining, by the one or more processors, a current view region of a portion of the whole slide image file at a user interface; (a) determining, by the one or more processors, a tile status for each tile of the one or more tiles within a current buffer region; (b) subdividing, by the one or more processors, buffering requirements associated with one or more tiles within the current buffer region into one or more buffering transactions, wherein each buffering transaction corresponds to at least one tile of the one or more tiles within the current buffer region that has a cached tile status; and (c) rendering, at the user interface, each tile of the one or more tiles within the current view region with an already buffered tile status for viewing by a user, among others.

Figure 2:
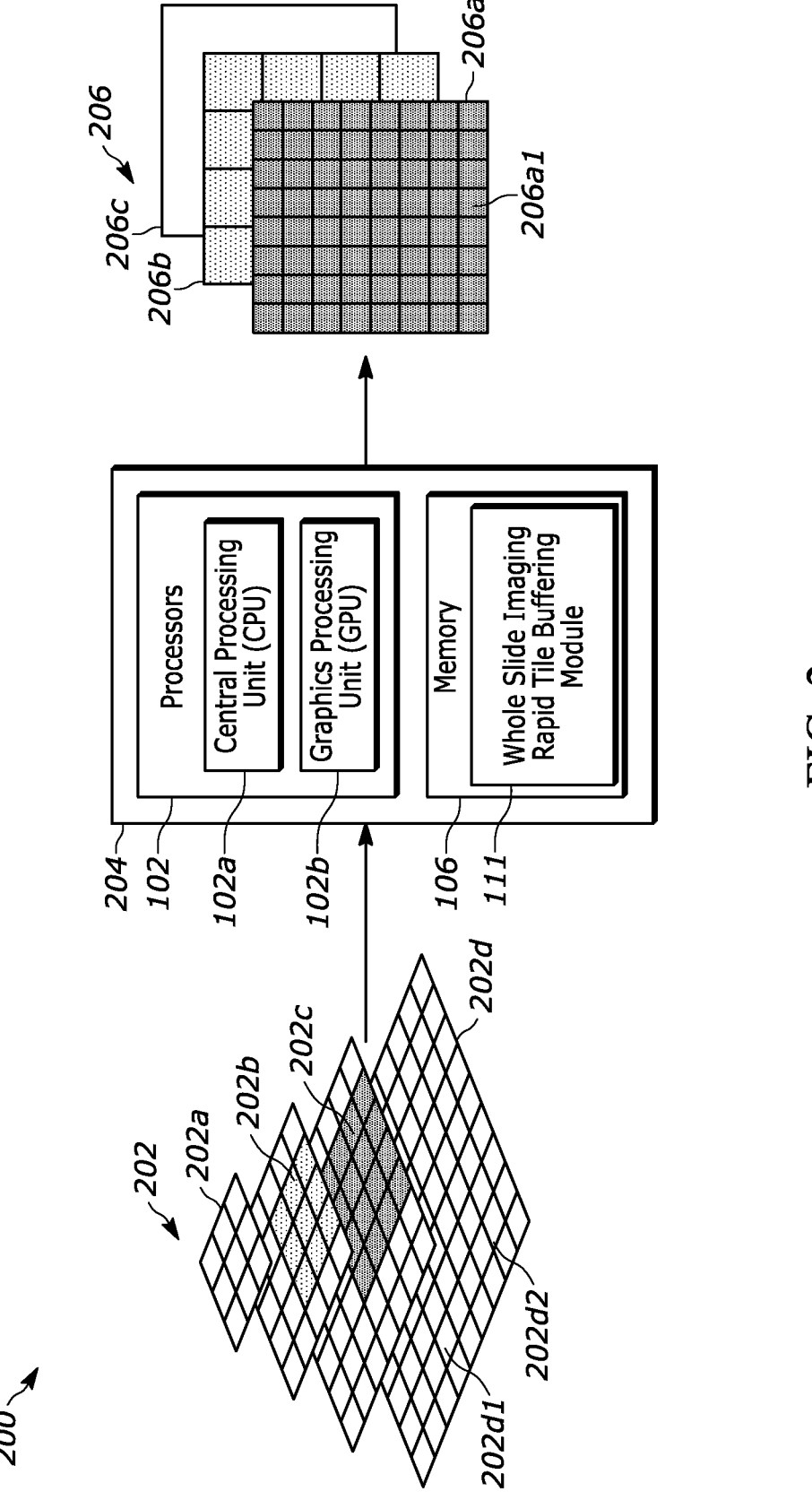
FIG. 2 illustrates an example workflow for dividing and subdividing WSI files into tiles that may be rendered by a graphics processing unit (GPU) utilizing several components from the example computing environment of FIG. 1, and in accordance various aspects disclosed herein.
Figure 3:
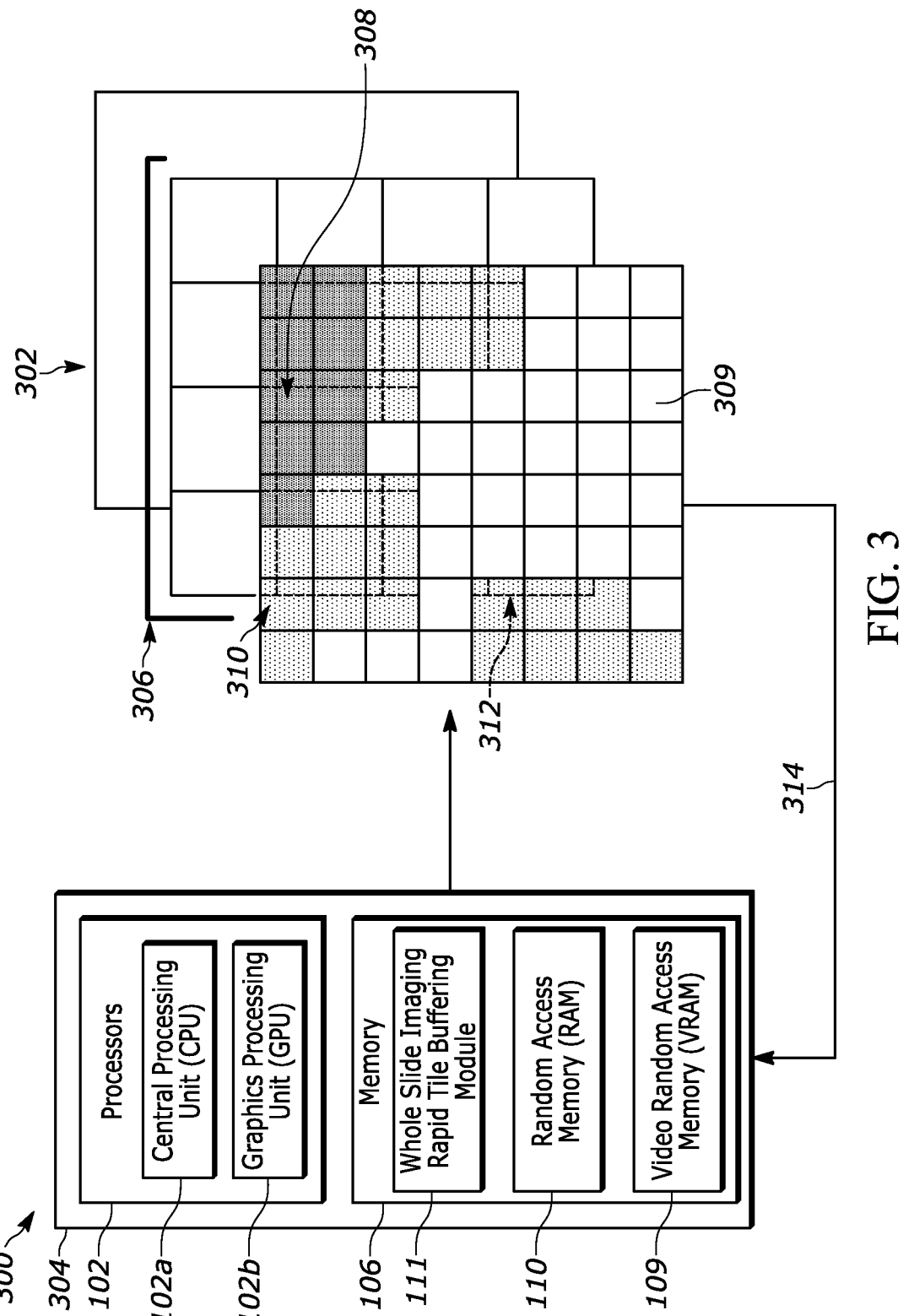
FIG. 3 illustrates an iterative buffer sequence for mapping and uploading tiles to a GPU for rendering when a user includes the tiles in a current view region of a user interface, in accordance with various aspects disclosed herein.
Figure 4:
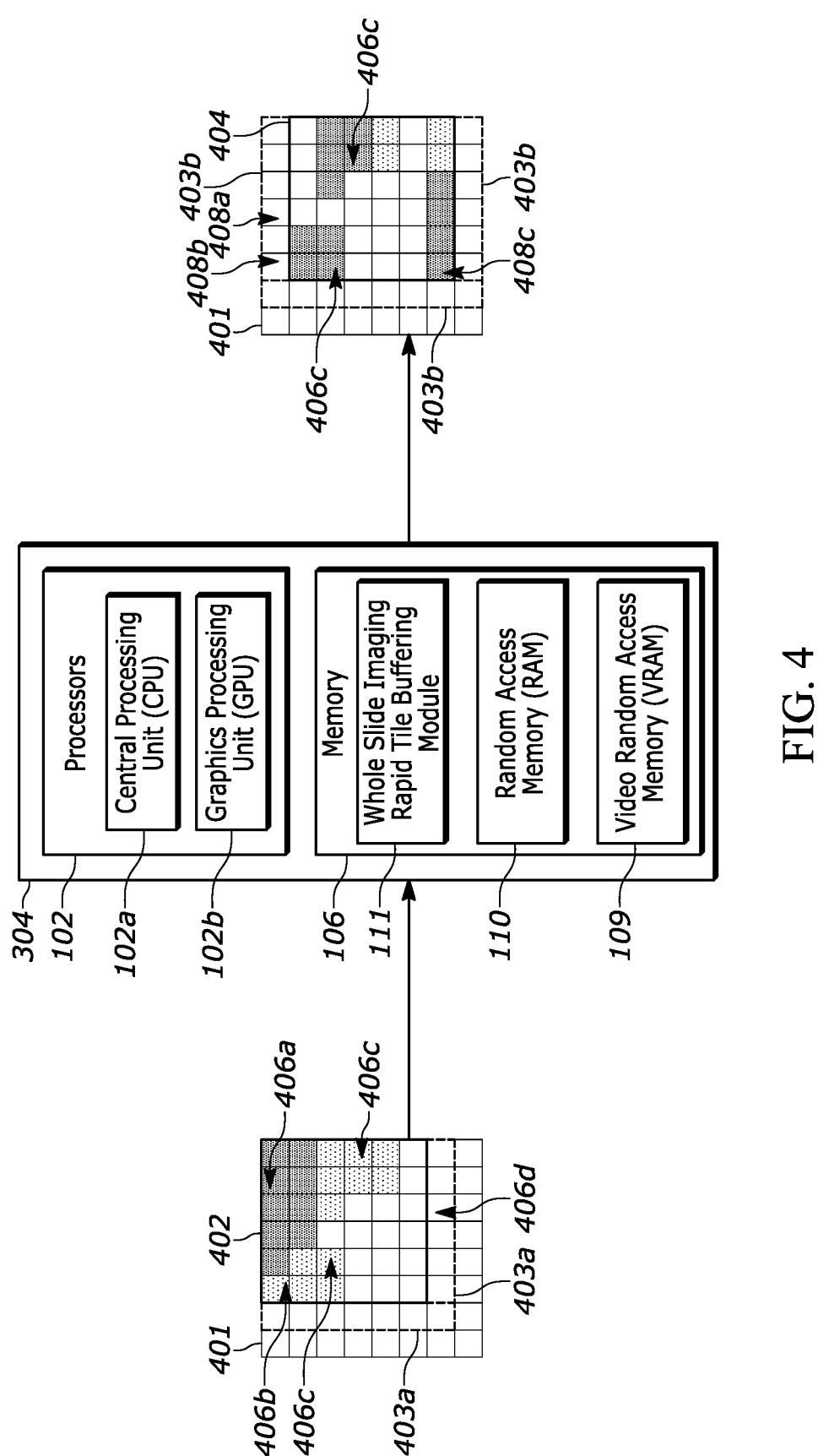
FIG. 4 illustrates the iterative buffer sequence actively updating tiles for mapping, uploading, and/or rendering as a user shifts the current view region from a first location to a second location, in accordance with various aspects disclosed herein.

To provide a general understanding of the system(s)/components utilized in the techniques of the present disclosure, FIG. 1 illustrates an example computing environment for improved whole slide imaging (WSI), in accordance various aspects disclosed herein. Thereafter, FIGS. 2-4 illustrate example workflows for dividing and subdividing WSI files into tiles (FIG. 2), and an iterative buffer sequence for mapping and uploading tiles to a GPU (FIG. 3) and actively updating tiles for mapping, uploading, and/or rendering when a user includes the tiles in a current view region of a user interface (FIG. 4). Finally, FIG. 5 illustrates an example method for improved WSI, in accordance various aspects disclosed herein.

In any event, FIG. 1 illustrates an example computing environment 100 for improved WSI. As illustrated in FIG. 1, the example computing environment 100 may include a user computing device 101 that includes a processor 102, a user interface 104, and a memory 106. The processor 102 may have a central processing unit (CPU) 102a and a graphics processing unit (GPU) 102b. Generally speaking, both the CPU 102a and the GPU 102b may access the memory 106 to execute instructions included therein, such as the operating system 108, the whole slide imaging rapid tile buffering module 111, and/or to access data or instructions stored in the random-access memory (RAM) 110 and/or included in the other data 112. The CPU 102a may be configured to execute a wide range of tasks stored in the memory 106, such as dividing and sub-dividing whole slide images into resolution layers and/or tiles. The GPU 102b may be configured to perform tasks associated with rendering the whole slide images for viewing by a user. Of course, it should be understood that the CPU 102a and the GPU 102b may perform additional tasks not described herein. Further, it should be appreciated that the example computing environment 100 is merely an example and that alternative or additional components are envisioned.

The user computing device 101 further includes a user interface 104 configured to present/receive information to/from a user. As shown in FIG. 1, the user interface 104 may include a display screen 104*a* and I/O components 104*b* (e.g., ports, capacitive or resistive touch sensitive input panels, keys, buttons, lights, LEDs). According to some aspects, a user may access the user computing device 101 via the user interface 104 to review outputs from the processors 102 (e.g., executing the whole slide imaging rapid tile buffering module 111), adjust a current view region of a particular whole slide image, make various selections, and/or otherwise interact with the user computing device 101 and the example computing environment 100. In particular, the user may interact with the I/O components 104*b* in order to adjust a current view region to view a new portion of a particular whole slide image. As discussed further herein, the processors 102 may receive an indication of the new portion of the particular whole slide image that is featured on the current view region, and may respond accordingly by executing instructions included as part of the whole slide imaging rapid tile buffering module 111 to adjust the tiles/resolution layers presented on the display screen 104*a* to the user to reflect the new portion of the particular whole slide image.

Generally speaking, and as discussed further herein, the whole slide imaging rapid tile buffering module 111 may cause the processors 102 to access/process two distinct components: slide layers 110*a* and rendering layers 109*a*. The slide layers 110*a* may be broadly defined by the digital images captured by the imaging device 114 that are included as part of the whole slide image files received by the user computing device 102. The rendering layers 109*a* may be broadly defined by the screen resolution and size of the user's display (e.g., display screen 104*a*). In particular, both the slide layers 110*a* and the rendering layers 109*a* may include corresponding tiles (e.g., sub-divided portions of the respective layers 110*a*, 109*a*), and the tiles of the rendering layers 109*a* may render tiles of the slide layers 110*a*. Moreover, as a user adjusts the position of the current view region over a particular slide image, the particular tiles of the slide layers 110*a* included in the current view region may change, whereas the tiles of the rendering layers 109*a* may remain constant because they are defined by the size of the display screen instead of the portion of a slide image being viewed. As illustrated in FIG. 1, the slide layers 110*a* may be stored on the RAM 110, and the rendering layers 109*a* may be stored on the VRAM 109.

The memory 106 may store an operating system 108 capable of facilitating the functionalities as discussed herein, the RAM 110, the whole slide imaging rapid tile buffering module 111, as well as other data 112. The other data 112 may include a set of applications configured to facilitate the functionalities as discussed herein, and/or may include other relevant data, such as display formatting data, etc. It should be appreciated that one or more other applications are envisioned. Moreover, it should be understood that any processor (e.g., processor 102), user interface (e.g., user interface 104), and/or memory (e.g., memory 106) referenced herein may include one or more processors, one or more user interfaces, and/or one or more memories.

In any event, the memory 106 may include one or more forms of volatile and/or non-volatile, fixed and/or removable memory, such as read-only memory (ROM), electronic programmable read-only memory (EPROM), the RAM 110, the video random access memory (VRAM) 109, erasable electronic programmable read-only memory (EEPROM), and/or other hard drives, flash memory, MicroSD cards, and others.

The example computing environment 100 also includes an imaging device 114 that is configured to capture images of tissue samples that are mounted on slides. When a tissue sample is mounted on a slide, the imaging device 114 may capture multiple images of the tissue sample at, for example, multiple resolutions. The imaging device 114 may also capture multiple high-resolution images of the slide that feature a portion of the slide that is less than the whole of the slide, such that the device 114 captures enough high-resolution images of the slide to stitch together a complete, high-resolution image of the slide. For example, as previously mentioned, the imaging device 114 may capture multiple images (e.g., tiles) of the slide, so that the tiles may thereafter be stitched together to form the high-resolution image of the slide. It should be understood that the imaging device 114 may capture any suitable number of images of the slide at any suitable resolution.

Moreover, in some aspects, the example system 100 may perform the functionalities as discussed herein as part of a "cloud" network or may otherwise communicate with other hardware or software components within the cloud to send, retrieve, or otherwise analyze data. Thus, it should be appreciated that the example computing environment 100 may be/include a distributed cluster of computers, servers, machines, or the like. In this implementation, a user may utilize the distributed example computing environment 100 as part of an on-demand cloud computing platform. Accordingly, when the user interfaces with the example computing environment 100 (e.g., by capturing images of a slide using the imaging device 114, uploading captured images to the user computing device 101), the example computing environment 100 may actually interface with one or more of a number of distributed computers, servers, machines, or the like, to facilitate the described functionalities.

For example, the user computing device 101 may communicate and interface with an external server 116 via a network(s). The external server 116 may be, for example, a remote storage location for the digital images of slides, and may receive the captured digital images of each slide from the user computing device 101 after analysis from a pathologist (or other specialist) and/or directly from the imaging device 114.

Further in these aspects, the network(s) used to connect the user computing device 101 to the imaging device 114 and/or the external server 116 may support any type of data communication via any standard or technology (e.g., GSM, CDMA, TDMA, WCDMA, LTE, EDGE, OFDM, GPRS, EV-DO, UWB, Internet, IEEE 802 including Ethernet, WiMAX, Wi-Fi, Bluetooth, and others). Moreover, the imaging device 114 and/or the external server 116 may include a memory as well as a processor, and the memory may store an operating system capable of facilitating some/all of the functionalities as discussed herein.

Additionally, it is to be appreciated that a computer program product in accordance with an aspect may include a computer usable storage medium (e.g., standard RAM, an optical disc, a universal serial bus (USB) drive, or the like) having computer-readable program code embodied therein, wherein the computer-readable program code may be adapted to be executed by the processor(s) 102 (e.g., working in connection with the operating system 108) to facilitate the functions as described herein. In this regard, the program code may be implemented in any desired language, and may be implemented as machine code, assembly code, byte code, interpretable source code or the like (e.g., via Golang, Python, Scala, C, C++, Java, Actionscript, Objective-C, Javascript, CSS, XML). In some aspects, the computer program product may be part of a cloud network of resources.

In any event, FIG. 2 illustrates an example workflow 200 for dividing and subdividing WSI files into tiles that may be rendered by a GPU (e.g., GPU 102*b*) utilizing several components from the example computing environment 100 of FIG. 1, and in accordance various aspects disclosed herein. The example workflow 200 includes a set of whole slide image tiles 202 that represent a slide at various levels of resolution, a slide image file processing component set 204, and a set of visible image tiles 206 rendered by the GPU 102*b*. The set of whole slide image tiles 202 may be generated by the CPU 102*a* after receiving a slide image file (not shown) containing images of a particular slide captured by an imaging device (e.g., imaging device 114). The slide image file processing component set 204 may include components of the example computing environment 100 of FIG. 1 that are configured to perform actions relevant to the set of whole slide image tiles 202 and/or the set of visible image tiles 206. The set of visible image tiles 206 include image tiles that are rendered by the GPU 102*b* for display/viewing to/by a user (e.g., a pathologist) during diagnosis of conditions represented in the tissue sample featured in the slide images. In certain aspects, the set of whole slide image tiles 202 may correspond to the slide layers 110*a*, and the set of visible image tiles 206 may correspond to the rendering layers 109*a*. Each of the actions described in reference to FIG. 2 may be performed in accordance with instructions included as part of, for example, the whole slide imaging rapid tile buffering module 111.

Generally speaking, the CPU 102*a* may receive a slide image file (not shown) containing multiple images of the slide captured by the imaging device (e.g., imaging device 114). The CPU 102*a* may divide the images in the image file into the resolution layers 202*a*-*d*, and may then sub-divide the individual resolution layers 202*a*-*d* into tiles. For example, the CPU 102*a* may receive the image file corresponding to the slide represented in the resolution layers 202*a*-*d*, the CPU 102*a* may divide the image file into the respective resolution layers 202*a*-*d*, and may then sub-divide the resolution layers 202*a*-*d* into tiles, such as tiles 202*d*1, 202*d*2 of the fourth resolution layer 202*d*. In certain aspects, each tile (e.g., tiles 202*d*1, 202*d*2) is a 256×256 pixel sub-image of the corresponding resolution layer 202*a*-*d*, and as a result, the number of tiles corresponding to each resolution layer 202*a*-*d* is directly proportional to the number of pixels within the respective resolution layer 202*a*-*d*.

For example, the first resolution layer 202*a* may represent the slide a lowest relative level of resolution, the second resolution layer 202*b* may represent the slide a second lowest relative level of resolution, the third resolution layer 202*c* may represent the slide a second highest relative level of resolution, and the fourth resolution layer 202*d* may represent the slide a highest relative level of resolution. Accordingly, in this example, the first resolution layer 202*a* may include a first number of tiles, the second resolution layer 202*b* may include a second number of tiles that is greater than the first number of tiles, the third resolution layer 202*c* may include a third number of tiles that is greater than the second number of tiles, and the fourth resolution layer 202*d* may include a fourth number of tiles that is greater than the third number of tiles. Typically, four resolution layers may be utilized as part of the present techniques, but it should be understood that any suitable number of resolution layers may be utilized.

When the CPU 102*a* has divided and sub-divided the slide image file into resolution layers 202*a*-*d* that each contain multiple tiles (e.g., tiles 202*d*1, 202*d*2), the GPU 102*b* may render the tiles for viewing by a user. In particular, the tiles may be drawn by the GPU 102*b* using image abstractions of the tissue sample represented in the tiles, and the image abstractions may contain a subsampling of the image data included in any particular tile and/or set of nearby tiles. Broadly speaking, when the GPU 102*b* renders image tiles for display to a user, the high-resolution layer tiles may be displayed with priority over lower-resolution layer tiles, but the lower-resolution layer tiles may be rendered with priority over high-resolution layer tiles in order to ensure that at least a low-resolution tile is available for display to a user.

As an example, the GPU 102*b* may render tiles corresponding to the lowest resolution layer 202*a* first, and if any overlapping tiles in all of the higher resolution layers 202*b*-*d* are unavailable for rendering (e.g., unbuffered), then the unavailable tiles from the higher resolution layers 202*b*-*d* become transparent, and the GPU 102*b* may render a corresponding tile from the lowest resolution layer 202*a*. Further in this example, if a tile in a high resolution layer 202*c*-*d* is unavailable for rendering, but a corresponding tile from the second resolution layer 202*b* is available for rendering, then the unavailable tiles from the higher resolution layers 202*c*-*d* become transparent, and the GPU 102*b* may render the corresponding tile from the second resolution layer 202*b*. In this manner, the GPU 102*b* may prioritize high-resolution tiles for display, and may prioritize lower-resolution tiles for rendering to ensure that at least a low-resolution tile is available for display to a user.

In order for the GPU 102*b* to perform the above-described rendering sequence of image tiles, the image tiles may be mapped, via a directory, to GPU images when in use. In particular, each tile (e.g., tiles 202*d*1, 202*d*2) within each resolution layer 202*a*-*d* may receive a cache address in local RAM (e.g., RAM 110). When a respective tile receives a cache address, the cached, decompressed image tile becomes available for immediate GPU 102*b* buffering transactions. Moreover, the RAM 110 may be issued on demand when computing resources are needed. Such on-demand issuance of memory resources may typically be referenced as "lazy-instantiation," where the creation of a computer object is delayed until a first use of the computer object, thereby reducing the overhead of the corresponding computer program. Regardless, the whole slide imaging rapid tile buffering module 111 may also instruct the GPU 102*b* to utilize/access an additional temporary file cache (not shown) for decompressed image data of the image tiles, in order to reduce decompression latency.

In addition to mapping the image tiles to local RAM 110, the whole slide image rapid tile buffering module 111 may cause allocation of the VRAM (e.g., VRAM 109) for the visible images drawn by the GPU 102*b*. Unlike the RAM 110 allocation for the image tiles that is proportional to the size of the resolution layers (e.g., 202*a*-*d*), the memory allocation in the VRAM 109 may be proportional to the application window size and screen resolution, and may be almost independent of the slide image size. As previously mentioned, the visible images are GPU 102*b* abstractions of drawn image pixels that are immediately visible to the pathologist. In this manner, only as much VRAM 109 is allocated as is needed to render visible high-resolution tiles and low-resolution tiles. In particular, the whole slide imaging rapid tile buffering module 111 may cause the GPU 102*b* and VRAM 109 visible image resources to be dynamically allocated and reallocated as necessary to image tiles, as part of the buffering and rendering sequences (described further herein). The association between a tile index within the resolution layer that includes indices corresponding to each tile in the respective resolution layer and the GPU 102b imaging resource is mapped in a directory (not shown) stored in memory 106. This mapping between the tile index and the GPU 102b image resource may be dynamically updated as tiles enter and exit the current view region of the user's display screen (e.g., display screen 104a), and the GPU 102b resources of exiting tiles may be reallocated to entering tiles, as part of the buffer loop sequence (described further herein).

As an example, while the user is viewing a current view region that includes certain slide tiles (e.g., tiles 202c, 202b), the slide tiles that are cached may be buffered to an available (e.g., unmapped) rendering tile (e.g., rendering tile 206a1) included in a respective rendering layer (e.g., rendering layers 206a, 206b, 206c) in order to be rendered for display to the user. In particular, the GPU 102b may utilize a first rendering tile (e.g., included in a first rendering tile layer 206a) to render a first slide tile in a corresponding resolution layer 202a-d. However, when the user adjusts the current view region to include different slide tiles, the GPU 102b may continue to utilize the first rendering tile to render a second slide tile in a corresponding resolution layer 202a-d that is different from the first slide tile.

Thus, as indicated in the above example and as previously mentioned, the number of slide layers/tiles (e.g., resolution layers 202a-d, tiles 202d1, 202d2) may be fixed by the whole slide image file, and as a result, may not be consistent between layers (e.g., there might be 4 slide layers that respectively include tile numbers of 48, 400, 4000, 10000). The rendering layers 206a-c may be defined by the size of the view screen (e.g., display screen 104a), such that there may only be as many rendering tiles (e.g., rendering tile 206a1) as can fit on the display screen 104a when it is fully zoomed out, and there may be a different number of rendering layers 206a-c than resolution layers 202a-d. For example, there may be only 2 rendering layers (e.g., just rendering layers 206a, 206b), and the rendering layers 206a-b may be/include 2×400 rendering tile layers stored in VRAM 109.

FIG. 3 illustrates an iterative buffer sequence 300 for mapping and uploading tiles to a GPU (e.g., GPU 102b) for rendering when a user includes the tiles in a current view region of a user interface (e.g., user interface 104), in accordance with various aspects disclosed herein. Generally speaking, the iterative buffer sequence 300 involves fragmenting the tiles that are currently viewable on a user's display screen (e.g., display screen 104a) into small batches of tiles with different statuses in order to handle rendering, uploading, and/or buffering the tiles, as necessary. In order to accomplish this fragmentation and rendering, uploading, and/or buffering, the iterative buffer sequence 300 may include multiple rendering layers 302 that are utilized by the buffer sequence components 304 to buffer and render tiles of the resolution layers (e.g., resolution layers 202a-d).

The sequence 300 may first include capturing a current view region of the slide image on a user's display, as represented by 306. Generally, 306 may represent the dimensions of the user's display screen (e.g. display screen 104a), which the buffer sequence components 304 may utilize to divide the display screen into the multiple rendering layers 302, and more specifically, rendering tiles (e.g., rendering tile 206a1) within each rendering layer 302. Each rendering layer 302 may correspond to computing resources of the GPU 102b/VRAM 109 that are utilized to render image tiles from the resolution layers 202a-d.

In any event, a user thread may update the current view region, and then the tile status for each tile included in a current buffer region is assessed to determine whether or not each respective tile included in the current buffer region is ready for rendering. Broadly, the current view region may correspond to the dimensions of the display screen 104a, and the current buffer region may include the current view region along with additional tiles around the current view region to account for a user adjusting the current view region during processing actions of the buffer sequence components, as described herein in reference to FIG. 4. Moreover, the amount of additional tiles included as part of the current buffer region may vary in accordance with the resolution layer in which the additional tiles are included. As a simple example, the current view region may include 10×10 high-resolution image tiles and 4×4 lower-resolution image tiles, and the current buffer region may include 11-12×11-12 high-resolution image tiles and 6-7 lower-resolution image tiles centered over the current view region. In this manner, the buffer sequence components 304 may actively prepare for the user to adjust the current view region by preparing (e.g., buffering) image tiles that are outside of the current view region that have not yet been buffered without consuming an excessive amount of processing bandwidth.

As previously mentioned, each respective tile included in the current view region may include a tile status that indicates what actions must be taken in order to render the respective tile. Namely, each respective tile may have (i) an un-cached tile status indicating that the associated tile is not yet loaded into the RAM 110, (ii) a cached tile status indicating that the associated tile is loaded into the RAM 110 and not yet buffered for uploading to the GPU 102b, or (iii) an already buffered tile status indicating that the associated tile is buffered and loaded to the GPU 102b for rendering at the user interface. Thus, the associated tile status for a respective tile indicates at least a next step that must be accomplished before the respective tile may be rendered at the user interface.

When the tile statuses are assessed, the sequence 300 may then include identifying respective tiles within the current buffer region that include a cached tile status to begin buffering these tiles, as represented by the patterning in rendering tiles 308. In any event, when the image tiles having the cached tile status and that are aligned with the rendering tiles 308 are queued for buffering, these image tiles may be uploaded to the GPU 102b, the GPU 102b may perform high-quality subsampling of the image tiles, and the image tiles may then be made available for rendering. These image tiles that are aligned with the rendering tiles 308 may generally represent a relatively small number of tiles that are immediately relevant to the user (e.g., pathologist) viewing the slide images, such that these processing tasks may be performed quickly and the processing resources required to perform these tasks may be released to handle other tasks.

While each image tile aligned with rendering tiles 308 in the current buffer region with a cached tile status is queued for buffering, other tiles within the current view/buffer region with other tile statuses may be temporarily ignored by the buffer sequence components 304. More specifically, any respective tiles in the current view region that have an already buffered tile status, such as image tiles represented by the patterning within rendering tile 309, and/or any respective tiles in the current view region that have an un-cached tile status, such as image tiles represented by the patterning within rendering tile 310, may be excluded from this initial buffering operation corresponding to the image tiles represented by the patterning in rendering tiles 308. Further, the respective tiles within the current view region with an un-cached tile status, such as image tiles represented by the patterning within rendering tile 310, may have their caching and loading to the RAM 110 prioritized.

Nevertheless, when the image tiles corresponding to rendering tiles 308 are processed by the GPU 102*b*, the sequence 300 may include issuing any image tiles corresponding to the rendering tiles 310 within the current view/buffer region with an un-cached tile status to loader/worker threads with high priority, thereby enabling the image tiles corresponding to rendering tiles 310 to skip ahead to the front of the load queue for the threads. As these image tiles corresponding to rendering tiles 310 are not mapped to the GPU 102*b*, these image tiles may not be rendered for viewing, and as a result, the space occupied by these tiles in the current view region may be transparent, allowing a rendered tile from a lower-resolution layer to be displayed, as indicated by the lower resolution rendering layer 312. As previously mentioned, low-resolution tiles may be given priority over high-resolution tiles for buffering, and such low-resolution tiles may interrupt the buffering of high-resolution tiles in order to ensure that at least a low-resolution tile is available for rendering to a user. Thus, high-resolution tiles may be transparent when not mapped, and the underlying low-resolution tiles may provide partial visibility during any lag experienced when caching and/or buffering of high-resolution tiles.

Thereafter, the iterative buffer sequence 300 may include issuing all buffered tiles to the render thread for rendering to the user's display (e.g., display screen 104*a*). This rendering step may conclude a particular iteration of the sequence 300, which may iteratively repeat any suitable number of times in order to cache, buffer, and render tiles for the current view region, as represented by the iterative loop 314. During this iterative buffer sequence 300, the processors may iteratively check for updates to the current view region in order to enable dynamic reloading/reallocation of processing/memory resources to cache, buffer, and render the most relevant tiles for viewing by a user. Moreover, it should be appreciated that the iterative buffer sequence 300 may include an identical sub-sequence (e.g., a nested loop) for each rendering layer 302 that includes always checking and completing the caching, buffering, and rendering of lower-resolution layers (e.g., resolution layers 202*a-d*) between each iteration of the sequence 300 for a higher-resolution layer. In this manner, the sequence 300 ensures that lower-resolution tiles are always available for display in the event that a higher-resolution tile is unavailable for display.

Further, as previously mentioned, the iterative buffer sequence 300 may generally operate on a dedicated thread in a continuous nested loop. This particular construction enables the buffer sequence components 304 to divide buffering tasks into multiple small requests based upon the current tile status of each tile within the current view region. The tile cache is a shared resource that is read by the iterative buffer sequence 300 and modified by the numerous loader/worker threads. The iterative buffer sequence 300 does not pause or wait on any external loading, and thus executes fast enough to cycle multiple times between individual frame renderings of the tiles.

FIG. 4 illustrates the buffer sequence components 304 performing the iterative buffer sequence 300 to actively update tiles for mapping, uploading, and/or rendering as a user shifts the current view region from a first location to a second location, in accordance with various aspects disclosed herein. As illustrated in FIG. 4, the current view region may be positioned over a first location 402 (also referenced herein as "current view region 402"), and as a user scrolls and/or otherwise manipulates the digital image 401, the user may shift the current view region to be positioned over a second location 404 (also referenced herein as "current view region 404").

As previously described, the current view region may correspond to a portion of the digital image 401 that is currently positioned for display on a user's display device (e.g., display screen 104*a*). Moreover, the tiles within the current view region represented in FIG. 4 may be rendering tiles that include patternings representative of a stage of processing (e.g., caching, buffering, rendering) corresponding to an image tile, over which, the rendering tile is positioned as part of the current view region. However, for ease of discussion, these rendering tiles may be referenced herein as "tiles".

In the first location, the current view region 402 includes multiple image tiles that are in various stages relative to the iterative buffering sequence 300. For example, the image tiles in tiles 406*a* may be newly buffered and ready for rendering, the image tiles in tile 406*b* may be loaded but irrelevant after the current view region moves from the first location 402 to the second location 404, the image tiles in tiles 406*c* may not yet be loaded at the first location 402, and the image tile 406*d* may be a previously loaded tile that is not buffered because it is not within the first location 402 of the current view region 402.

In particular, at the first location 402, the image tile 406*d* may represent a portion of the current buffer region 403*a* that extends beyond the current view region 402. The current buffer region 403*a* may include, for example, each of the image tiles that are adjacent to and/or otherwise nearby image tiles that are included as part of the current view region 402, such as the image tile 406*d*. If the user does not move the current view region 402, then the buffer sequence components 304 may perform the iterative buffering sequence 300 as described above in order to eventually cache, buffer, and/or render each of the image tiles in tiles 406*a-d*.

However, when the user shifts the current view region 402 from the first location 402 to the second location 404, the tile status and resource allocation of these image tiles may change. For example, the image tiles 408*a* may no longer be relevant because they are not within the current view region 404, and as a result, the image tiles 408*a* may have any space on the VRAM 109 that was previously occupied by these image tiles 408*a* re-allocated (e.g., deleted) to make space for more immediately relevant tiles that are within the current view region 404. Similarly, the image tile 408*b* may not be buffered during a subsequent iteration of the iterative buffering sequence 300 once the user shifts the current view region 402 from the first location 402 to the second location 404 because the image tile 408*b* is not within the current view region 404.

Moreover, at the second location 404, these image tiles 408*a, b* may represent a portion of the current buffer region 403*b* that extends beyond the current view region 404. The current buffer region 403*b* may include, for example, each of the image tiles that are adjacent to and/or otherwise nearby image tiles that are included as part of the current view region 404, such as the image tiles 408*a, b*. It should be appreciated that the current buffer regions 403*a*, 403*b* may include any suitable number of image tiles, and may extend any suitable distance away from the current view region 402, 404. For example, at a high-resolution layer (e.g., resolution layer represented by digital image 401), the current buffer regions 403*a*, 403*b* may include one to two additional image tiles extending away from each perimeter tile within the current view region 402, 404, and at a lower-resolution layer (e.g., lower resolution rendering layer 312) the current buffer regions may include three to five additional image tiles extending away from each perimeter tile within the current view region.

Of course, certain tiles may remain within and/or become included within the current view region after the user shifts the position of the current view region (e.g., from first location 402 to second location 404). For example, the image tiles in tiles 406*c* may remain in the current view region 404 after the user shifts the current view region 402, such that the image tiles in tiles 406*c* continue to be included as part of subsequent iterations of the iterative buffering sequence 300. In particular, after the user shifts the current view region 402 to the current view region 404, the image tiles in tiles 406*c* may be prioritized during a subsequent iteration of the iterative buffering sequence 300 in order to load/buffer these image tiles in tiles 406*c*. Similarly, the image tiles in tiles 408*c* may become included in the current view region 404 after the user shifts the current view region 402 to the current view region 404, such that the image tiles in tiles 408*c* become included as part of subsequent iterations of the iterative buffering sequence 300. These image tiles in tiles 408*c* may have been previously loaded during a prior iteration of the iterative buffering sequence 300, such that when the image tiles in tiles 408*c* become included in the current view region 404, a subsequent iteration of the iterative buffering sequence 300 may immediately buffer these image tiles in tiles 408*c*.

Thus, generally speaking, this dynamic updating of the current view region 402, 404 (e.g., via tile indices) in combination with the iterative buffering sequence 300 drastically minimizes buffering of outdated (e.g., no-longer visually relevant) tiles and maximizes bandwidth conservation. More specifically, the iterative buffering sequence 300 recaptures the most relevant view region (e.g., the current view region 402, 404) with each iteration, completely agnostic of any prior requests. The sequence 300 then re-requests priority caching of tiles that are still within the current view region but include an un-cached tile status, and allows any prior requests (even high-priority) to fall lower in the cache load-queue. Further, any tiles that have loaded as part of a prior view region but are not part of the current view region 402, 404 (e.g., within the current buffer regions 403*a*, 403*b*) may remain cached into RAM 110 for immediate use as needed in future view regions without wasting valuable buffering and subsampling bandwidth because they are not needed for the current view region 402, 404 rendering.

FIG. 5 illustrates an example method 500 for improved WSI, in accordance various aspects disclosed herein. For ease of discussion, many of the various actions included in the method 500 may be optional, and may be described herein as performed by or with the use of a processor (e.g., processor 102). However, it is to be appreciated that the various actions included in the method 500 may be performed by, for example, a specific processing unit (e.g., CPU 102*a*, GPU 102*b*) executing the whole slide imaging rapid tile buffering module 111, an external server (e.g., external server 116), and/or other suitable processors or combinations thereof.

The method 500 may include receiving, at one or more processors, a whole slide image file comprised of image data corresponding to a tissue sample, wherein the whole slide image file includes one or more resolution layers that each include one or more tiles (block 502). The whole slide image file may include any suitable number of images representing the tissue sample and/or any other suitable object. For example, the whole slide image file may include multiple images of the tissue sample at different resolutions, and the different resolution images may comprise multiple tiles that have been stitched together to form the higher-resolution composite image of the tissue sample.

In certain aspects, the method 500 may also include dividing, by the one or more processors, the whole slide image file into one or more resolution layers. For example, the CPU (e.g., CPU 102*a*) may receive the whole slide image file, and may proceed to divide the whole slide image file into the one or more resolution layers by determining a resolution for each image in the whole slide image file and/or aggregating the images with identical resolution together.

Moreover, in some aspects, the method 500 may include subdividing, by the one or more processors, each resolution layer of the one or more resolution layers into one or more tiles. In certain aspects, the CPU 102*a* may subdivide each resolution layer of the one or more resolution layers into one or more tiles based on a number of pixels included in a respective resolution layer. For example, the CPU 102*a* may proceed to sub-divide images from each resolution layer into one or more tiles by ensuring that each tile is 256×256 pixels in dimension. Thus, each resolution layer may be subdivided into a different number of tiles based on the overall number pixels available at any respective resolution layer. Namely, a very high-resolution layer may be subdivided into dozens of tiles, while a very low-resolution layer may be subdivided into only a few tiles.

In certain aspects, the method 500 may further include subdividing, by the one or more processors, each resolution layer of the one or more resolution layers into the one or more tiles using image abstractions of the tissue sample that contain a subsampling from the corresponding resolution layer. Further, in certain aspects, the method 500 may include subdividing, by the one or more processors, each resolution layer of the one or more resolution layers into the one or more tiles based on dimensions of a display screen of the user interface through which the user is viewing the whole slide image file. For example, the CPU 102*a* may subdivide the resolution layers based on the ultimate resolution in which the tiles may be displayed on the user's display screen (e.g., display screen 104*a*), and/or based on the dimensions in which the tiles may be displayed on the display screen 104*a* in order to ensure that the tiles are optimally configured for display on the specific display screen 104*a* utilized by the user to view the tiles.

In some aspects, the method 500 may further include dividing, by the one or more processors, a display screen (e.g., display screen 104*a*) used to display the user interface into one or more rendering layers (e.g., rendering layers 302). The one or more processors may then also subdivide each rendering layer of the one or more rendering layers into one or more rendering tiles. In these aspects, the one or more resolution layers may include a first number of layers, and the one or more rendering layers may include a second number of layers that is different from the first number of layers. In particular, the first number of layers may be four resolution layers, and the second number of layers may be two rendering layers. Of course, it should be appreciated that the resolution layers and the rendering layers may include any suitable number of layers.

In some aspects, the method 500 may further include assigning, by the one or more processors, a cache address in a local memory to each tile of the one or more tiles for each resolution layer of the one or more resolution layers. For example, each tile may receive a cache address in RAM (e.g., RAM 110) that allows the tiles to be quickly referenced for buffering to the GPU (e.g., GPU 102*b*).

The method 500 may further include determining, by the one or more processors, a current view region of a portion of the whole slide image file at a user interface (block 504). Additionally, the method 500 may include determining, by the one or more processors, a tile status for each tile of the one or more tiles within a current buffer region (block 506). In certain aspects, the method 500 may further include determining, by the one or more processors, a tile status for each tile of the one or more tiles within the current buffer region, wherein an un-cached tile status indicates that the associated tile is not yet loaded into a random access memory (RAM), the cached tile status indicates that the associated tile is loaded into the RAM and not yet buffered for uploading to a graphics processing unit (GPU), and the already buffered tile status indicates that the associated tile is buffered and loaded to the GPU for rendering at the user interface.

The method 500 may further include subdividing, by the one or more processors, buffering requirements associated with one or more tiles within the current buffer region into one or more buffering transactions (block 508). Generally, each buffering transaction may correspond to at least one tile of the one or more tiles within the current buffer region that has a cached tile status. More specifically, individual buffering transactions may include the CPU 102*a* or another processing resource buffering an image tile with a cached tile status to the GPU 102*b* (e.g., via VRAM 109), such that a rendering tile may subsequently render the image tile for viewing by a user.

In some aspects, each tile of the one or more tiles within the current buffer region may correspond to a high resolution layer of the one or more resolution layers. Further in these aspects, the method 500 may include subdividing, by the one or more processors, the buffering requirements (e.g., caching, buffering) associated with the one or more tiles within the current buffer region into one or more buffering transactions, such that each tile of one or more lower resolution tiles within the current buffer region that has a cached tile status is buffered prior to buffering each tile of the one or more tiles within the current buffer region that has a cached tile status. In this manner, and as previously discussed, the processors may prioritize the lower-resolution layers over the higher-resolution layers in order to ensure that at least a low resolution tile is available for display in the event that a high resolution tile is unavailable for display to a user.

In certain aspects, the method 500 may further include buffering, by the one or more processors, each tile of the one or more tiles within the current buffer region that has the cached tile status. In these aspects, the method 500 may then further include uploading, by the one or more processors, each buffered tile to a GPU (e.g., GPU 102*b*), and subsampling, by the GPU 102*b*, each buffered tile.

The method 500 may further include (c) rendering, at the user interface, each tile of the one or more tiles within the current view region with an already buffered tile status for viewing by a user (block 510). In certain aspects, the method 500 may further include detecting, by the one or more processors, that the user has adjusted the current view region to a new current view region of a new portion of the whole slide image file within the user interface. Further in these aspects, the method 500 may include designating, by the one or more processors, the current view region as a subsequent view region and the new current view region as the current view region. The method 500 may also include performing each of the steps included in blocks 506-510 based on the current view region.

In some aspects, wherein each tile of the one or more tiles within the current view region corresponds to a high resolution layer of the one or more resolution layers. Further in these aspects, the method 500 may include, responsive to at least one tile of the one or more tiles within the current view region having an un-cached tile status, rendering, at the user interface, at least a portion of a corresponding lower resolution tile with an already buffered tile status from a lower resolution layer of the one or more resolution layers for viewing by a user in place of the at least one tile.

ASPECTS OF THE PRESENT DISCLOSURE

1. A method for improved whole slide imaging (WSI), comprising: receiving, at one or more processors, a whole slide image file comprised of image data corresponding to a tissue sample, the whole slide image file including one or more resolution layers that each include one or more tiles; determining, by the one or more processors, a current view region of a portion of the whole slide image file at a user interface; (a) determining, by the one or more processors, a tile status for each tile of the one or more tiles within a current buffer region; (b) subdividing, by the one or more processors, buffering requirements associated with one or more tiles within the current buffer region into one or more buffering transactions, wherein each buffering transaction corresponds to at least one tile of the one or more tiles within the current buffer region that has a cached tile status; and (c) rendering, at the user interface, each tile of the one or more tiles within the current view region with an already buffered tile status for viewing by a user.

2. The method of aspect 1, further comprising: detecting, by the one or more processors, that the user has adjusted the current view region to a new current view region of a new portion of the whole slide image file within the user interface; designating, by the one or more processors, the current view region as a subsequent view region and the new current view region as the current view region; and performing each of steps (a)-(c) based on the current view region.

3. The method of any of aspects 1-2, wherein each tile of the one or more tiles within the current view region corresponds to a high resolution layer of the one or more resolution layers, and the method further comprises: responsive to at least one tile of the one or more tiles within the current view region having an un-cached tile status, rendering, at the user interface, at least a portion of a corresponding lower resolution tile with an already buffered tile status for viewing by a user in place of the at least one tile.

4. The method of any of aspects 1-3, wherein each tile of the one or more tiles within the current buffer region corresponds to a high resolution layer of the one or more resolution layers, and the method further comprises: subdividing, by the one or more processors, the buffering requirements associated with the one or more tiles within the current buffer region into one or more buffering transactions, such that each tile of one or more lower resolution tiles within the current buffer region that has a cached tile status is buffered prior to buffering each tile of the one or more tiles within the current buffer region that has a cached tile status.

5. The method of any of aspects 1-4, further comprising: dividing, by the one or more processors, a display screen used to display the user interface into one or more rendering layers; and subdividing, by the one or more processors, each rendering layer of the one or more rendering layers into one or more rendering tiles.

6. The method of aspect 5, wherein the one or more resolution layers includes a first number of layers, and the one or more rendering layers includes a second number of layers that is different from the first number of layers.

7. The method of any of aspects 1-6, further comprising: dividing, by the one or more processors, the whole slide image file into the one or more resolution layers; and subdividing, by the one or more processors, each resolution layer of the one or more resolution layers into one or more tiles based on a number of pixels included in a respective resolution layer.

8. The method of any of aspects 1-7, further comprising: assigning, by the one or more processors, a cache address in a local memory to each tile of the one or more tiles for each resolution layer of the one or more resolution layers.

9. The method of any of aspects 1-8, further comprising: buffering, by the one or more processors, each tile of the one or more tiles within the current buffer region that has the cached tile status; uploading, by the one or more processors, each buffered tile to a graphics processing unit (GPU); and subsampling, by the GPU, each buffered tile.

10. The method of any of aspects 1-9, further comprising: (a) determining, by the one or more processors, a tile status for each tile of the one or more tiles within the current buffer region, wherein an un-cached tile status indicates that the associated tile is not yet loaded into a random access memory (RAM), the cached tile status indicates that the associated tile is loaded into the RAM and not yet buffered for uploading to a graphics processing unit (GPU), and the already buffered tile status indicates that the associated tile is buffered and loaded to the GPU for rendering at the user interface.

11. A system for improved whole slide imaging (WSI), comprising: a user interface; a memory storing a set of computer-readable instructions; and a processor interfacing with the user interface and the memory, and configured to execute the set of computer-readable instructions to cause the processor to: receive a whole slide image file comprised of image data corresponding to a tissue sample, the whole slide image file including one or more resolution layers that each include one or more tiles, determine a current view region of a portion of the whole slide image file at a user interface, (a) determine a tile status for each tile of the one or more tiles within a current buffer region, (b) subdivide buffering requirements associated with one or more tiles within the current buffer region into one or more buffering transactions, wherein each buffering transaction corresponds to at least one tile of the one or more tiles within the current buffer region that has a cached tile status, and (c) render, at the user interface, each tile of the one or more tiles within the current view region with an already buffered tile status for viewing by a user.

12. The system of aspect 11, wherein the set of computer-readable instructions, when executed, further cause the processor to: detect that the user has adjusted the current view region to a new current view region of a new portion of the whole slide image file within the user interface; designate the current view region as a subsequent view region and the new current view region as the current view region; and perform each of steps (a)-(c) based on the current view region.

13. The system of any of aspects 11-12, wherein each tile of the one or more tiles within the current view region corresponds to a high resolution layer of the one or more resolution layers, and the set of computer-readable instructions, when executed, further cause the processor to: subdivide the buffering requirements associated with the one or more tiles within the current buffer region into one or more buffering transactions, such that each tile of one or more lower resolution tiles within the current buffer region that has a cached tile status is buffered prior to buffering each tile of the one or more tiles within the current buffer region that has a cached tile status; and responsive to at least one tile of the one or more tiles within the current view region having an un-cached tile status, render, at the user interface, at least a portion of a corresponding lower resolution tile with an already buffered tile status for viewing by a user in place of the at least one tile.

14. The system of any of aspects 11-13, wherein the set of computer-readable instructions, when executed, further cause the processor to: divide a display screen used to display the user interface into one or more rendering layers; and subdivide each rendering layer of the one or more rendering layers into one or more rendering tiles.

15. The system of aspect 14, wherein the one or more resolution layers includes a first number of layers, and the one or more rendering layers includes a second number of layers that is different from the first number of layers.

16. The system of any of aspects 11-15, wherein the set of computer-readable instructions, when executed, further cause the processor to: divide the whole slide image file into the one or more resolution layers; and subdivide each resolution layer of the one or more resolution layers into one or more tiles based on a number of pixels included in a respective resolution layer.

17. The system of any of aspects 11-16, wherein the set of computer-readable instructions, when executed, further cause the processor to: assign a cache address in a local memory to each tile of the one or more tiles for each resolution layer of the one or more resolution layers.

18. The system of any of aspects 11-17, wherein the set of computer-readable instructions, when executed, further cause the processor to: buffer each tile of the one or more tiles within the current buffer region that has the cached tile status; upload each buffered tile to a graphics processing unit (GPU); and cause the GPU to subsample each buffered tile.

19. The system of any of aspects 11-18, wherein the set of computer-readable instructions, when executed, further cause the processor to: (a) determine a tile status for each tile of the one or more tiles within the current buffer region, wherein an un-cached tile status indicates that the associated tile is not yet loaded into a random access memory (RAM), the cached tile status indicates that the associated tile is loaded into the RAM and not yet buffered for uploading to a graphics processing unit (GPU), and the already buffered tile status indicates that the associated tile is buffered and loaded to the GPU for rendering at the user interface.

20. A non-transitory computer-readable storage medium having stored thereon a set of instructions, executable by at least one processor, for improved whole slide imaging (WSI), the instructions comprising: instructions for receiving a whole slide image file comprised of image data corresponding to a tissue sample, the whole slide image file including one or more resolution layers that each include one or more tiles; instructions for determining a current view region of a portion of the whole slide image file at a user interface; instructions for determining a tile status for each tile of the one or more tiles within a current buffer region; instructions for subdividing buffering requirements associated with one or more tiles within the current buffer region into one or more buffering transactions, wherein each buffering transaction corresponds to at least one tile of the one or more tiles within the current buffer region that has a cached tile status; and instructions for rendering, at the user interface, each tile of the one or more tiles within the current view region with an already buffered tile status for viewing by a user.

ADDITIONAL CONSIDERATIONS

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding; and no unnecessary limitations should be understood therefrom, as modifications within the scope of the invention may be apparent to those having ordinary skill in the art.

What is claimed:

1. A method for improved whole slide imaging (WSI), comprising:
receiving, at one or more processors, a whole slide image file comprised of image data corresponding to a tissue sample, the whole slide image file including one or more resolution layers that each include one or more tiles;
determining, by the one or more processors, a current view region of a portion of the whole slide image file at a user interface;
(a) determining, by the one or more processors, a tile status for each tile of the one or more tiles within a current buffer region;
(b) subdividing, by the one or more processors, buffering requirements associated with one or more tiles within the current buffer region into one or more buffering transactions, wherein each buffering transaction corresponds to at least one tile of the one or more tiles within the current buffer region that has a cached tile status; and
(c) rendering, at the user interface, each tile of the one or more tiles within the current view region with an already buffered tile status for viewing by a user.

2. The method of claim 1, further comprising:
detecting, by the one or more processors, that the user has adjusted the current view region to a new current view region of a new portion of the whole slide image file within the user interface;
designating, by the one or more processors, the current view region as a subsequent view region and the new current view region as the current view region; and
performing each of steps (a)-(c) based on the current view region.

3. The method of claim 1, wherein each tile of the one or more tiles within the current view region corresponds to a high resolution layer of the one or more resolution layers, and the method further comprises:
responsive to at least one tile of the one or more tiles within the current view region having an un-cached tile status, rendering, at the user interface, at least a portion of a corresponding lower resolution tile with an already buffered tile status for viewing by a user in place of the at least one tile.

4. The method of claim 1, wherein each tile of the one or more tiles within the current buffer region corresponds to a high resolution layer of the one or more resolution layers, and the method further comprises:
subdividing, by the one or more processors, the buffering requirements associated with the one or more tiles within the current buffer region into one or more buffering transactions, such that each tile of one or more lower resolution tiles within the current buffer region that has a cached tile status is buffered prior to buffering each tile of the one or more tiles within the current buffer region that has a cached tile status.

5. The method of claim 1, further comprising:
dividing, by the one or more processors, a display screen used to display the user interface into one or more rendering layers; and
subdividing, by the one or more processors, each rendering layer of the one or more rendering layers into one or more rendering tiles.

6. The method of claim 5, wherein the one or more resolution layers includes a first number of layers, and the one or more rendering layers includes a second number of layers that is different from the first number of layers.

7. The method of claim 1, further comprising:
dividing, by the one or more processors, the whole slide image file into the one or more resolution layers; and
subdividing, by the one or more processors, each resolution layer of the one or more resolution layers into one or more tiles based on a number of pixels included in a respective resolution layer.

8. The method of claim 1, further comprising:
assigning, by the one or more processors, a cache address in a local memory to each tile of the one or more tiles for each resolution layer of the one or more resolution layers.

9. The method of claim 1, further comprising:
buffering, by the one or more processors, each tile of the one or more tiles within the current buffer region that has the cached tile status;
uploading, by the one or more processors, each buffered tile to a graphics processing unit (GPU); and
subsampling, by the GPU, each buffered tile.

10. The method of claim 1, further comprising:

(a) determining, by the one or more processors, a tile status for each tile of the one or more tiles within the current buffer region, wherein an un-cached tile status indicates that the associated tile is not yet loaded into a random access memory (RAM), the cached tile status indicates that the associated tile is loaded into the RAM and not yet buffered for uploading to a graphics processing unit (GPU), and the already buffered tile status indicates that the associated tile is buffered and loaded to the GPU for rendering at the user interface.

11. A system for improved whole slide imaging (WSI), comprising:

a user interface;

a memory storing a set of computer-readable instructions; and a processor interfacing with the user interface and the memory, and configured to execute the set of computer-readable instructions to cause the processor to:

receive a whole slide image file comprised of image data corresponding to a tissue sample, the whole slide image file including one or more resolution layers that each include one or more tiles, determine a current view region of a portion of the whole slide image file at a user interface, (a) determine a tile status for each tile of the one or more tiles within a current buffer region, (b) subdivide buffering requirements associated with one or more tiles within the current buffer region into one or more buffering transactions, wherein each buffering transaction corresponds to at least one tile of the one or more tiles within the current buffer region that has a cached tile status, and (c) render, at the user interface, each tile of the one or more tiles within the current view region with an already buffered tile status for viewing by a user.

12. The system of claim 11, wherein the set of computer-readable instructions, when executed, further cause the processor to:

detect that the user has adjusted the current view region to a new current view region of a new portion of the whole slide image file within the user interface;

designate the current view region as a subsequent view region and the new current view region as the current view region; and perform each of steps (a)-(c) based on the current view region.

13. The system of claim 11, wherein each tile of the one or more tiles within the current view region corresponds to a high resolution layer of the one or more resolution layers, and the set of computer-readable instructions, when executed, further cause the processor to:

subdivide the buffering requirements associated with the one or more tiles within the current buffer region into one or more buffering transactions, such that each tile of one or more lower resolution tiles within the current buffer region that has a cached tile status is buffered prior to buffering each tile of the one or more tiles within the current buffer region that has a cached tile status; and responsive to at least one tile of the one or more tiles within the current view region having an un-cached tile status, render, at the user interface, at least a portion of a corresponding lower resolution tile with an already buffered tile status for viewing by a user in place of the at least one tile.

14. The system of claim 11, wherein the set of computer-readable instructions, when executed, further cause the processor to:

divide a display screen used to display the user interface into one or more rendering layers; and subdivide each rendering layer of the one or more rendering layers into one or more rendering tiles.

15. The system of claim 14, wherein the one or more resolution layers includes a first number of layers, and the one or more rendering layers includes a second number of layers that is different from the first number of layers.

16. The system of claim 11, wherein the set of computer-readable instructions, when executed, further cause the processor to:

divide the whole slide image file into the one or more resolution layers; and subdivide each resolution layer of the one or more resolution layers into one or more tiles based on a number of pixels included in a respective resolution layer.

17. The system of claim 11, wherein the set of computer-readable instructions, when executed, further cause the processor to:

assign a cache address in a local memory to each tile of the one or more tiles for each resolution layer of the one or more resolution layers.

18. The system of claim 11, wherein the set of computer-readable instructions, when executed, further cause the processor to:

buffer each tile of the one or more tiles within the current buffer region that has the cached tile status;

upload each buffered tile to a graphics processing unit (GPU); and cause the GPU to subsample each buffered tile.

19. The system of claim 11, wherein the set of computer-readable instructions, when executed, further cause the processor to:

(a) determine a tile status for each tile of the one or more tiles within the current buffer region, wherein an un-cached tile status indicates that the associated tile is not yet loaded into a random access memory (RAM), the cached tile status indicates that the associated tile is loaded into the RAM and not yet buffered for uploading to a graphics processing unit (GPU), and the already buffered tile status indicates that the associated tile is buffered and loaded to the GPU for rendering at the user interface.

20. A non-transitory computer-readable storage medium having stored thereon a set of instructions, executable by at least one processor, for improved whole slide imaging (WSI), the instructions comprising:

instructions for receiving a whole slide image file comprised of image data corresponding to a tissue sample, the whole slide image file including one or more resolution layers that each include one or more tiles;

instructions for determining a current view region of a portion of the whole slide image file at a user interface;

instructions for determining a tile status for each tile of the one or more tiles within a current buffer region;

instructions for subdividing buffering requirements associated with one or more tiles within the current buffer region into one or more buffering transactions, wherein each buffering transaction corresponds to at least one tile of the one or more tiles within the current buffer region that has a cached tile status; and instructions for rendering, at the user interface, each tile of the one or more tiles within the current view region with an already buffered tile status for viewing by a user.

\* \* \* \* \*